US006180849B1

(12) United States Patent
Streuli et al.

(10) Patent No.: US 6,180,849 B1
(45) Date of Patent: Jan. 30, 2001

(54) TRANGENIC MICE WITH A DISRUPTION IN THE TIAR GENE

(75) Inventors: Michel Streuli, Brookline; Paul Anderson, Belmont, both of MA (US); Andreas Beck, Lucerne (CH)

(73) Assignee: Dana-Farber Cancer Institute, Inc., Boston, MA (US)

(*) Notice: Under 35 U.S.C. 154(b), the term of this patent shall be extended for 0 days.

(21) Appl. No.: 09/039,999

(22) Filed: Mar. 17, 1998

Related U.S. Application Data

(60) Provisional application No. 60/040,931, filed on Mar. 17, 1997, and provisional application No. 60/050,102, filed on Jun. 20, 1997.

(51) Int. Cl.$^7$ .......................... C12N 15/85; C12N 15/86; G01N 33/00; A01K 67/00
(52) U.S. Cl. ...................... 800/18; 800/3; 800/8; 800/9; 800/10; 800/13; 800/14; 435/325
(58) Field of Search ................ 435/325; 800/3, 800/8, 13, 14, 15, 16, 17, 18

(56) References Cited

U.S. PATENT DOCUMENTS 5,340,935    8/1994    Anderson et al. .................. 536/23.5

OTHER PUBLICATIONS

Mullins et al., J. Clin. Invest., vol. 98, pp. S37–S41, 1996.*
Moreadith et al., J. Mol. Med., vol. 75, pp. 208–216, 1997.*
Moens et al, Development, vol. 119, pp. 459–499, 1993/*
Beck et al. Nucleic Acids Res. vol. 24, pp. 3829–3835, 1996.*
Capecchi et al. Sci. Amer. vol. 270, pp. 34–41, 1994.*
Beck et al., "RNA–binding protein TIAR is essential for primordial germ cell development", Proc. Natl. Acad. Sci. USA 95:2331–2336, 1998.
Beck et al., "Structure, tissue distribution and genomic organization of the murine RRM–type . . . ", Nucleic Acids Research 24:3829–3835, 1996.
Dember et al., "Individual RNA Recognition Motifs of TIA–1 and TIAR Have Different RNA . . . ", The Journal of Biological Chemistry 271:2783–2788, 1996.
Kawakami et al., "Identification and functional characterization of a TIA–related nucleolysin", Proc. Natl. Acad. Sci. USA 89:8681–8685, 1992.

Taupin et al., "The RNA–binding protein TIAR is translocated from the nucleus to the cytoplasm . . . ", Proc. Natl. Acad. Sci. USA 92:1629–1633, 1995.
Tian et al., "Fas–activated Serine/Threonine Kinase (FAST) Phosphorylates TIA–1 during . . . ", J. Exp. Med. 182:865–874, 1995.
Tian et al., "A Polyadenylate Binding Protein Localized to the Granules of Cytolytic Lymphocytes . . . ", Cell 67:629–639, 1991.
Anderson, P. et al., "A Monoclonal Antibody Reactive Reactive with a 15–kDa Cytoplasmic Granule–Associated Protein Defines A Subpopulation of CD8+ T Lymphocytes," J. Immunol. 144:2 574–582 (1990).
Anderson, P. et al., "Monoclonal Antibodies Reactive With The T Cell Receptor Chain: Production And Characterization Using A New Method," J. Immunol. 143:6 1899–194 (1989).
Bradley, A. et al., "Modifying The Mouse: Design And Desire," Biotech. vol. 10:534–539 (1992).
Brand, S. et al., "Developmentally–Regulated Drosophila Gene Rox8 Encodes An RRM–Type RNA Binding Protein Structurally Related To Human TIA–1–Type Nucleolysins," Nucleic Acids Research 21:16 3699–3704 (1993).
Cappecchi, M.R., "Targeted Gene Replacement," Sci. Amer. 270:3 34–41 (1994).
Freshney, R.I., "Culture of Animal Cells," New York, NY: Alan R. Liss, Inc. 2nd Edition, pp. 270, 277–280, 287 and 290 (1987).
Kawakami, A. et al., "A polyadenylate Binding Protein Localized To The Granules of Cytolytic Lymphocytes Induces DNA Fragmentation In Target Cells," Cell 6:3 629–638 (1991).

* cited by examiner

Primary Examiner—John L. LeGuyader
Assistant Examiner—Michael C. Wilson
(74) Attorney, Agent, or Firm—Fish & Richardson P.C.

(57) ABSTRACT

The invention features transgenic non-human mammals containing a mutation in one or both alleles of the endogenous TIAR gene, and cell lines derived from some of these mammals. The mammals and cell lines of the invention can be employed to identify compounds useful in treating infertility, obesity, neurological disorders, and ovarian sex cord stromal tumors.

22 Claims, 3 Drawing Sheets

TRANSGENIC MICE WITH A DISRUPTION IN THE TIAR GENE

CROSS REFERENCE TO RELATED APPLICATIONS

Under 35 USC §119(e)(1), this application claims the benefit of prior U.S. Provisional Application Ser. No. 60/040,931, filed Mar. 17, 1997, and U.S. Provisional Application Ser. No. 60/050,102, filed Jun. 20, 1997.

STATEMENT AS TO FEDERALLY SPONSORED RESEARCH

This invention was funded in part by National Institutes of Health Grant No. AI 33600. The government has certain rights in the invention.

FIELD OF THE INVENTION

This invention relates to transgenic animals.

BACKGROUND OF THE INVENTION

Figure 1:
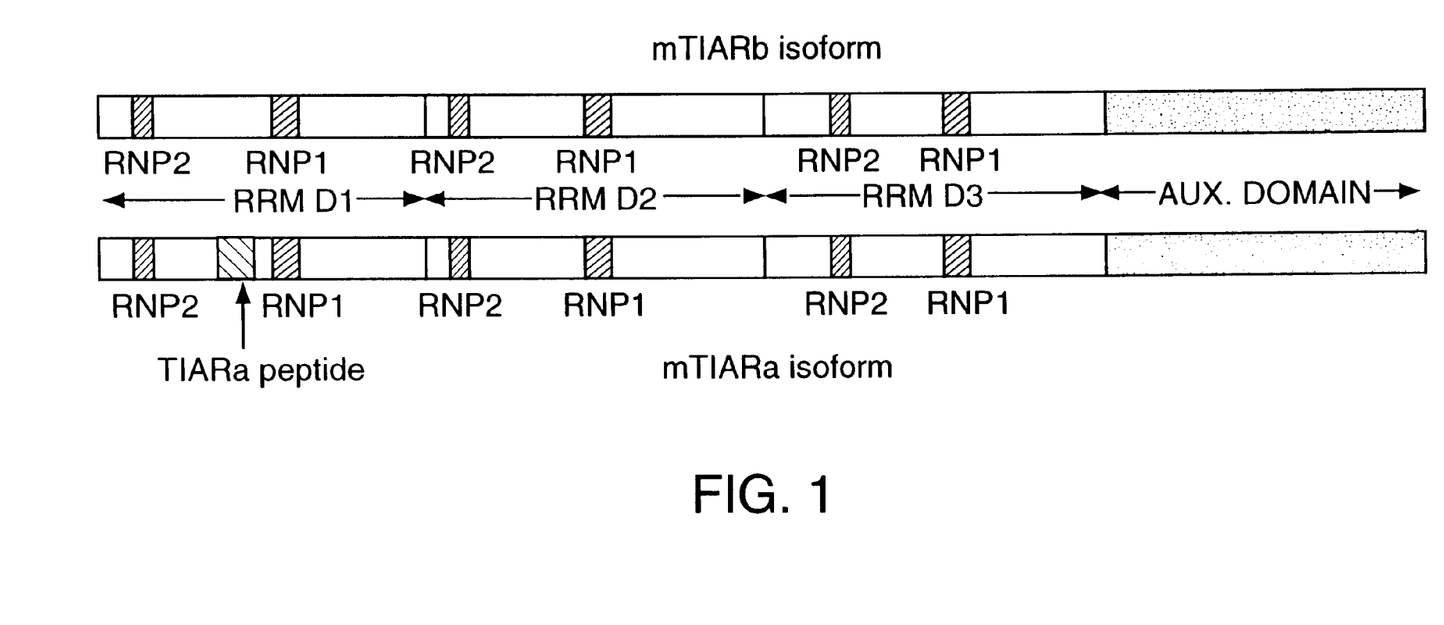
FIG. 1 is a schematic diagram showing the genomic structure of the two murine TIAR isoforms.

Several families of RNA-binding proteins are involved in a variety of fundamental cellular processes including RNA splicing, polyadenylation, RNA transport, and translation. Members of the RNA recognition motif (RRM)/ribonucleoprotein (RNP) family contain one to four approximately 100 amino acid long RRM domains in association with various auxiliary domains. TIAR is a RRM protein that is comprised of three N-terminal RRM domains and a C-terminal auxiliary domain (Beck et al., Nucleic Acid Research 24: 3829–3835, 1996; Dember et al., J. Biol. Chem 271: 2783–2788, 1996; Taupin et al., Proc. Natl. Acad. Sci. USA 92: 1629–1633, 1995; Tian et al., Cell 67: 629–639, 1991). Murine TIAR is predominantly expressed in brain, testis, and spleen. At least two isoforms of the protein are generated by alternative splicing (FIG. 1).

SUMMARY OF THE INVENTION

The invention features transgenic non-human mammals (e.g., rodents such as mice and rats) all diploid cells of which contain a mutation in one or both alleles of the endogenous TIAR gene. The mutation can, for example, be a deletion, an insertion, or a nucleotide substitution. It can also be a translocation involving one or more exons, introns or transcription regulatory regions (e.g., a promoter) of the gene. If the mutation reduces the expression or activity level of the protein encoded by the mutated gene (all isoforms included) by more than 80% relative to the unmutated TIAR gene, the mutation is called a null mutation, and the mouse harboring the mutation is a knockout mouse. A homozygous TIAR null mutation has been found to cause partial lethality, infertility, obesity and neurological disorders in mice.

Also embraced by the present invention are cell lines derived from these transgenic non-human mammals. These cell lines can be of any cell origin (e.g., primordial germ cell, fibroblast, ovarian cell, or neuron).

Transgenic mice homozygous for TIAR null mutation are infertile. One cause of infertility in these mice is the degeneration of primordial germ cells (PGCs). Thus, within the present invention is also a method of identifying fertility-enhancing compounds by use of TIAR-deficient transgenic mice. In this method, an appropriate amount of a test compound is first administered to TIAR-deficient mice. Survival of PGCs in these mice is then examined. Enhanced survival of these PGCs as compared to PGCs of control TIAR-deficient mice which have not been exposed to the test compound is an indication that the test compound is capable of enhancing fertility of a mammal.

Fertility-enhancing compounds can also be identified by use of PGCs derived from TIAR-deficient mice (e.g., in the form of primary cell cultures or cell lines). In particular, the PGCs can be obtained from these mice (e.g., from the genital ridges of these mice) at around day 11. To test a compound for its fertility-enhancing ability, the cultured PGCs are first contacted with an appropriate amount of the compound for an appropriate duration of time. Subsequently, the growth rate, life span, differentiation, or any other appropriate growth or metabolic parameter of the PGCs is examined by standard techniques. For instance, growth rate can be determined by the amount of radioactive nucleotides incorporated into replicating genomic DNA, or by the number of cells generated by cell division. Differentiation of these PGCs, on the other hand, can be assessed by change of protein expression pattern or morphology known to occur during normal PGC development. Increased growth rate, life span, and/or differentiation of the PGCs as compared to control PGCs which have not been treated with the test compound is an indication that the compound is capable of enhancing fertility of a mammal.

Female TIAR-deficient mice develop ovarian sex cord stromal tumors as they age. Thus, ovarian sex cord stromal tumor cells derived from these mice can be used to screen for chemotherapeutic compounds useful in treating ovarian cancer such as ovarian sex cord stromal tumors. To do so, these cells are contacted with a candidate compound, and the growth rate of the cells is examined, where a decrease in the growth rate as compared to an untreated control indicates that the compound inhibits the growth of ovarian sex cord stromal tumor cells. The compound can also be administered directly to a female TIAR-deficient mouse, and a delay, prevention, or even reversal of the development of ovarian sex cord stromal tumor indicates that the compound can be used to treat or prevent ovarian sex cord stromal tumors.

TIAR-deficient mice are underweight at birth but become obese at the age of approximately 2 to 4 months. The leptin level in these mice is abnormally high, and the mice tend to consume a larger amount of food than normal mice. Thus, to identify compounds that are capable of reducing body weight of an obese mammal, one can administer a test compound to TIAR-deficient transgenic mice after they become obese. After an appropriate duration of time (e.g., one to four weeks), the average body weight of these mice is compared to that of control mice which have not been exposed to the compound. A significant decrease (e.g., at least 20%, or even 50%) of the average body weight as compared to control is an indication that the compound is useful in reducing the body weight of an obese mammal. Similarly, the ability of a test compound to prevent excessive weight gain in these mice can be tested by beginning administration prior to the onset of obesity. Alternatively, one can determine the leptin level or the eating pattern of the compound-treated mice. Normalization of the leptin level or eating pattern (e.g., the amount of food consumption) will indicate that the test compound can be used to treat obesity or certain eating disorders.

TIAR-deficient mice also have certain neurological disorders. For instance, the mice are unusually nervous. Using these mice, a skilled artisan can identify compounds useful in treating anxiety in humans.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice of the present invention. All publications and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

DETAILED DESCRIPTION OF THE INVENTION

I. Transgenic Non-Human Mammals

Transgenic non-human mammals (e.g., mice, rats, rabbits, guinea pigs, sheep, swine, goats, cows and non-human primates such as chimpanzees and monkeys) containing a TIAR gene mutation in all of their diploid cells can be obtained by well known methods. In general, the mutation is introduced into target cells, e.g., ES cells or oocytes, via injection or transfection of a targeting DNA construct. The construct contains a genomic segment of the TIAR gene with the desired mutation in place. Subsequently, the injected oocytes are implanted into pseudopregnant foster females. Alternatively, the transfected ES cells are injected into appropriate blastocysts and then the blastocysts are implanted into foster females. The resulting mutation-containing offspring are identified. From these founder animals, distinct animal lines can be produced by breeding with wild-type animals. The heterozygotes so produced are then bred to obtain homozygotes. If the mutation is cell- or embryonic-lethal, no mature homozygotes will be obtained. If the mutation causes infertility, the homozygotes cannot be propagated.

In addition to the above mutations which are transmitted through the germline, one can also generate a stage- or tissue-specific deletional mutation in a non-human mammal. This mammal is made such that it contains (1) a pair of lox sites in an endogenous TIAR allele, bracketing a region of the gene that is desired to be deleted; and (2) a transgene encoding the cre recombinase under the control of a stage- or tissue-specific promoter. When the cre expression is activated at a proper stage during the animal's development (e.g., upon administration to the animal a compound capable of activating the promoter), or at the proper tissue of the animal, the two lox sites will undergo recombination, thereby deleting the intervening TIAR gene sequence.

The transgenic non-human mammals of the invention can serve as animal models for infertility, obesity, or ovarian cancer. Therapeutic compounds useful in treating one of these conditions can be screened by using the transgenic mammals or cell lines derived from these mammals. For instance, a candidate compound can be administered to a female TIAR-deficient mammal that has developed an ovarian sex cord stromal tumor, where a reduction in the size of the tumor as compared to an untreated control indicates that the compound can be used to treat ovarian sex cord stromal tumors.

The following example describes the generation of a transgenic mouse line that contains a null mutation on one or both alleles of the endogenous TIAR gene. This example is meant to illustrate, but not limit, the animals and methods of the present invention. Other suitable modifications and adaptations of the variety of conditions and parameters normally encountered in creating and analyzing transgenic animals are within the spirit and scope of the present invention.

EXAMPLE

TIAR-Deficient Mice (1) Knockout Strategy

Figure 2:
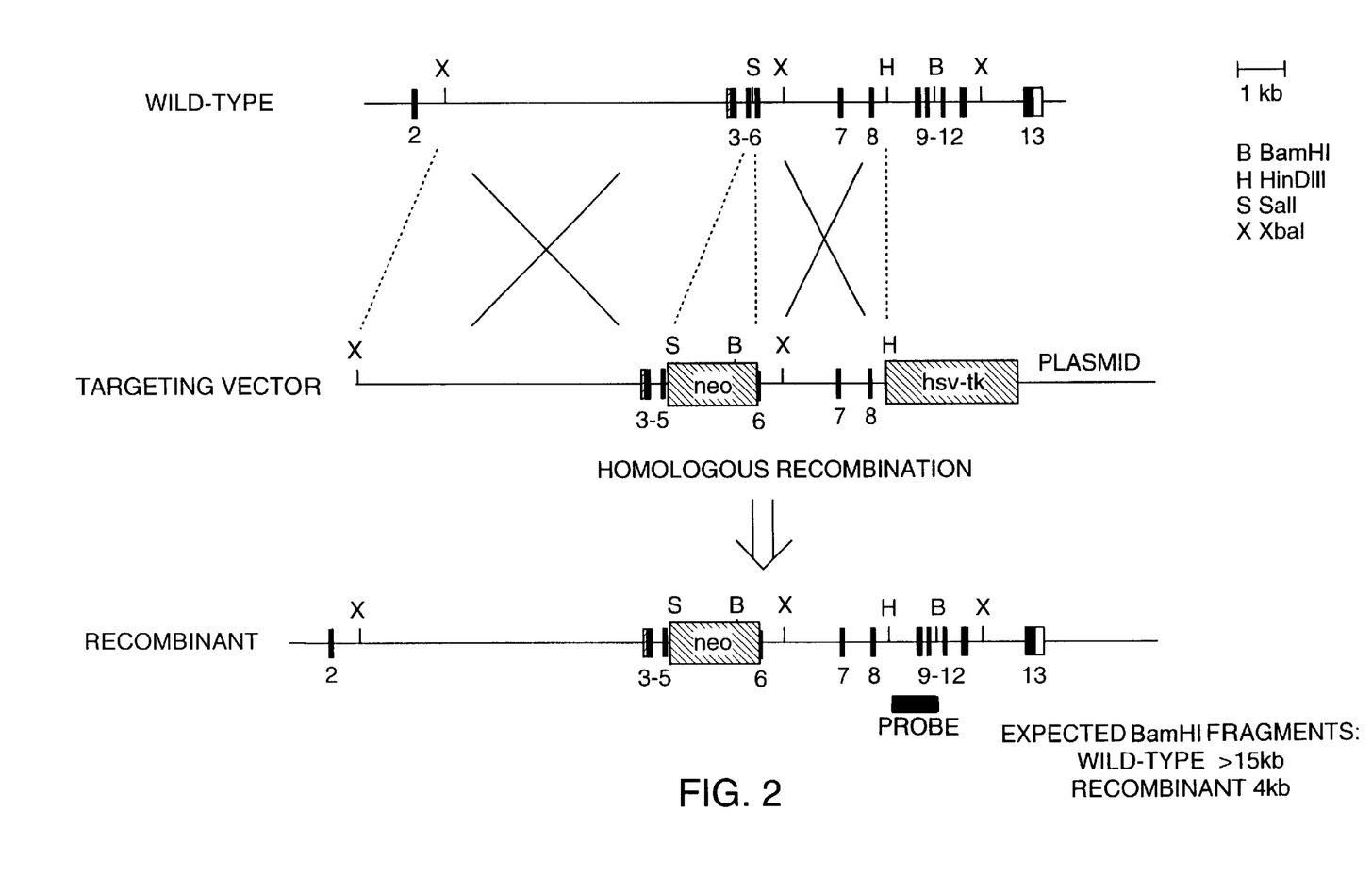
FIG. 2 is a schematic diagram showing the gene targeting strategy for generating TIAR-deficient mice.

The TIAR knockout construct contained a genomic segment of the murine TIAR gene that encompassed exons 2–8 (FIG. 2). To disrupt the expression of intact TIAR protein (both isoforms a and b), the neomycin phosphotransferase (neo) gene was inserted between exons 5 and 6 in the construct. Following transfection into ES cells, the knockout construct would undergo homologous recombination with one (or both) endogenous TIAR allele, resulting in integration of the neo gene between exons 5 and 6 in the allele. Transfectants could be selected for in a neomycin-containing culture medium.

However, integration of the knockout construct into the targeted locus through homologous recombination is a much rarer event than random integration of the construct into the mouse genome. Thus, selecting transfectants for mere neomycin-resistance will yield a high percentage of false positive. To conveniently eliminate transfectants that have randomly integrated the knockout construct, a herpes thymidine kinase (hsv-tk) gene was included in a non-targeting region of the knockout construct. As a result, transfectants that had undergone random integration would carry the intact hsv-tk gene and die in a gancyclovir-containing medium. Transfectants that had undergone homologous recombination did not contain any plasmid sequences that were outside the targeting region, and would therefore survive in the gancyclovir medium.

(2) Construction of the knockout construct

A knockout construct was prepared based on the pSP73 plasmid. This construct contains a 5' homology region (the XbaI-SalI genomic fragment encompassing exons 3–5; approximately 6.5 kb) and a 3' homology region (the EcoRV-HindIII genomic fragment encompassing part of exon 6 and extending through exon 8; approximately 2.5 kb) (FIG. 2). The neo gene under the control of a PGK (i.e., phosphoglycerate kinase) promoter was inserted between these two homology regions. A PGK-thymidine kinase cassette was ligated to the 3' end of the 3' homologous region.

(3) Homologous recombination at the TIAR locus

The linearized knockout construct was transfected into D3 ES cells. Other ES cell lines such as the J1 cell line may also be used. ES cells were cultured on a layer of neo-resistant (neo$^r$) embryonic fibroblast (EF) cells, which were prepared from E14 mouse embryos from a transgenic mouse carrying the neo gene (available from GenParm International, Mountain View, Calif.) and γ-irradiated before use.

For transfection, 25 µg of the construct linearized by EcoRI was added to $10^7$ ES cells suspended in 1 ml of medium. Electroporation of 0.8 ml aliquots was carried out under conditions optimized for transfection of a single copy of neo (at 25 mF, 400 volts, and at room temperature). Transfected ES cells were plated onto 10 cm petri dishes containing neo$^r$ EF cells without any drug selection. After 24 hrs of culture, G418 was added at 150 μg/ml to the transfected cells to select for colonies expressing neo. After an additional 48 hours, gancyclovir selection (2 μM) was initiated to select against colonies expressing hsv-tk.

Approximately 750 resistant colonies were expanded and analyzed by Southern blotting in order to identify clones in which the targeted homologous recombination event had indeed occurred. Probes used for the Southern analysis could hybridize to either the targeted region or sequences flanking the targeted region. For instance, a 0.9 kb genomic fragment covering exons 9–10 was used (FIG. 2). Hybridization of the BamHI-digested genomic DNA with this probe would show a fragment of more than 15 kb in size from the wild type locus and a fragment of 4 kb in size from the targeted locus.

(4) Generation of Chimeras Carrying the TIAR Mutation

ES cells carrying the TIAR mutation were injected into C57BL/6 blastocysts. Typically, twenty to twenty-five ES cells were injected per blastocyst. Injected blastocysts were transferred to the uterus of pseudopregnant Swiss-Webster mice. Germ-line transmission of one of the clones was obtained on further crossing of male chimeras with C57BL/6 females. Transmission of the tiar$^-$ allele (i.e., the TIAR gene allele containing the null mutation) through the germ line was demonstrated by Southern blot analysis of DNA from offspring of mice derived from the tiar$^{+/-}$ ES cells.

(5) Protein Analysis tiar$^{-/-}$ ES cell lines were derived from tiar$^{+/-}$ ES cells grown in 0.3 mg/ml G418 (Mortensen et al., Mol. Cell. Biol. 12:2391–2395, 1992). For protein analysis, tiar$^{-/-}$ ES cells were lysed in a buffer containing 1% Nonidet P-40, 150 mM NaCl, 50 mM Tris-HCl (Ph 8.0), 1 Mm EDTA, 1 Mm phenylmethylsulfonyl fluoride, 10 μg/ml aprotinin, and 10 μg/ml leupeptin. Samples were sonicated, and insoluble material was removed by centrifugation (10 minutes at 10,000×g). Proteins were resolved by 14% SDS/PAGE under reducing conditions, transferred to Immobilon P membrane (Millipore), and blotted with 1 μg/ml anti-TIAR 6E3 mAb. Antibody was detected with protein A/G-horseradish peroxidase (Pierce) and the chemiluminescence reagent luminol (DuPont/NEN).

(6) Southern Blot Analysis

Tail biopsies, kidneys, or yolk sacs were subjected to proteinase K digestion for 10–16 hours at 55° C. in a buffer containing 50 mM Tris-HCl (pH 8.5), 20 mM EDTA, 10 mM NaCl, 0.5% SDS and 0.5 mg/ml Proteinase K. Genomic DNA was recovered by phenol extraction and precipitation, and about 20 μg of genomic DNA digested with EcoRI was used for Southern blot analysis.

(7) Histology and Immunohistochemistry

For histology analysis, tissues or embryos were fixed in 10% buffered formalin (Sigma), embedded in paraffin, sectioned, and stained with hematoxylin and cosin according to standard procedures. For immunohistochemical analysis, sections (7 μM thick) were deparaffinized, rehydrated, and treated with antigen unmasking solution (Vector Laboratories). Sections were incubated for 1 hour with 10% horse serum and 5% bovine serum albumin (BSA) in phosphate buffered saline (PBS) and then for 30 minutes with 5 μg/ml anti-TIAR mAb 3E6 with 10% horse serum and 5% BSA in PBS. Sections were washed in PBS adjusted to 0.5 M NaCl, and primary mAb was detected with the VECTA STAIN ELITE ABC Peroxidase Kit (Vector Laboratories) and counterstained with Gill's hematoxylin. To detect GCNA1 antigen, sections were incubated for 20 minutes in PBS with 1.5% horse serum and then for 30 minutes with undiluted hybridoma supernatant conditioned with mAb against GCNA1 and washed in PBS. For alkaline phosphatase staining (Ginsburg et al., Development 110:521–528, 1990), embryos were obtained at E11.5 (day 0.5=day of finding a copulation plug) and stained for alkaline phosphatase activity during a 20 minute period at room temperature in a buffer containing 25 mM sodium tetraborate, 3.5 mM MgCl$_2$, 0.1 mg/ml sodium α-naphthylphosphate, and 0.1 mg/ml Fast Red TR salt (Sigma).

(8) In vitro Methylcellulose Assay for ES Cell Proliferation

For the in vitro methylcellulose proliferation assay, ES cells were dissociated by trypsinization followed by 6 passages through a 20-gauge needle. ES cells were then suspended in ES cell media [DMEM supplemented with 15% fetal calf serum, 1× penicillin-streptomycin solution (GIBCO/BRL), 2 mM L-glutamine, 0.1 mM MEM nonessential amino acid solution (GIBCO/BRL), 0.1 mM 2-mercaptoethanol, and 1% (wt/vol) methylcellulose (Fluka)] with or without the addition of 1,000 units of leukemia inhibitory factor (LIF; GIBCO/BRL) per ml. Cells were plated into nontreated, 96-well plates at about 1,000 cells in 0.15 ml per well. To measure cell proliferation at different days after cell plating, 1 μCi (1 Ci=37 GBq) [$^3$H]thymidine in 25 μl of ES cell media was added per well, and after 9 hours of incubation, the cells were harvested, and [$^3$H]thymidine incorporation was determined. Assays were done in triplicate with two independent tiar$^{-/-}$ and two independent control cell lines. The two tiar$^{-/-}$ ES cell clones were derived from independent tiar$^{+/-}$ ES clones by selection in 0.3 mg/ml G418 (Mortensen et al., Mol. Cell. Biol. 12:2391–2395, 1992). As control, two ES cell lines were used, one of which had undergone selection in 0.3 mg/ml G418.

(9) Phenotype of Homozygous TIAR Null Mutation i) Partial Lethality

Mice heterozygous for the tiar$^-$ allele were mated. Genotypes of the offspring were determined with respect to the TIAR locus at one week after birth. Of 165 offspring, 49 were wild type (30%); 107 were heterozygous (64%); and only 9 were homozygous (5%). Thus, according to the Mendelian principle of inheritance, the survival rate of mice homozygous for TIAR null mutation was only 17% (i.e., 5%:30%). The survival rate for the homozygous mice decreased to 14% at two to three weeks of age. However, mortality was not progressive beyond this point, and surviving tiar$^{-/-}$ mice lived beyond 12 months of age.

To investigate the cause of lethality among the homozygotes, embryos generated by breeding heterozygous mice were analyzed for genotype. At embryonic day 10.5 to 12.5 (E10.5–12.5), the numbers of tiar$^{-/-}$, tiar$^{+/-}$, and tiar$^{+/+}$ embryos were 19, 105, and 57, respectively; thus, only 33% (19/57) of the expected number of tiar$^{-/-}$ embryos were identified. Similarly, at E13.5–18.5 and E14.5–18.5, only 38% (tiar$^{-/-}$:tiar$^{+/-}$:tiar$^{+/+}$=15:77:40) and 50% (tiar$^{-/-}$:tiar$^{+/-}$:tiar$^{+/+}$=11:43:22) of the expected numbers of tiar$^{-/-}$ embryos were identified, respectively. These results indicate that more than 50% of the homozygous embryos died in utero. Slightly less than half of the remaining homozygous embryos survived to adulthood.

ii) Significant weight change

Weight measurements of embryos demonstrated that tiar$^{-/-}$ embryos were smaller than their tiar$^{+/-}$ or tiar$^{+/+}$ littermates at all embryonic stages examined. This size discrepancy persisted until they reached maturity at about 6 weeks of age.

Figure 3:
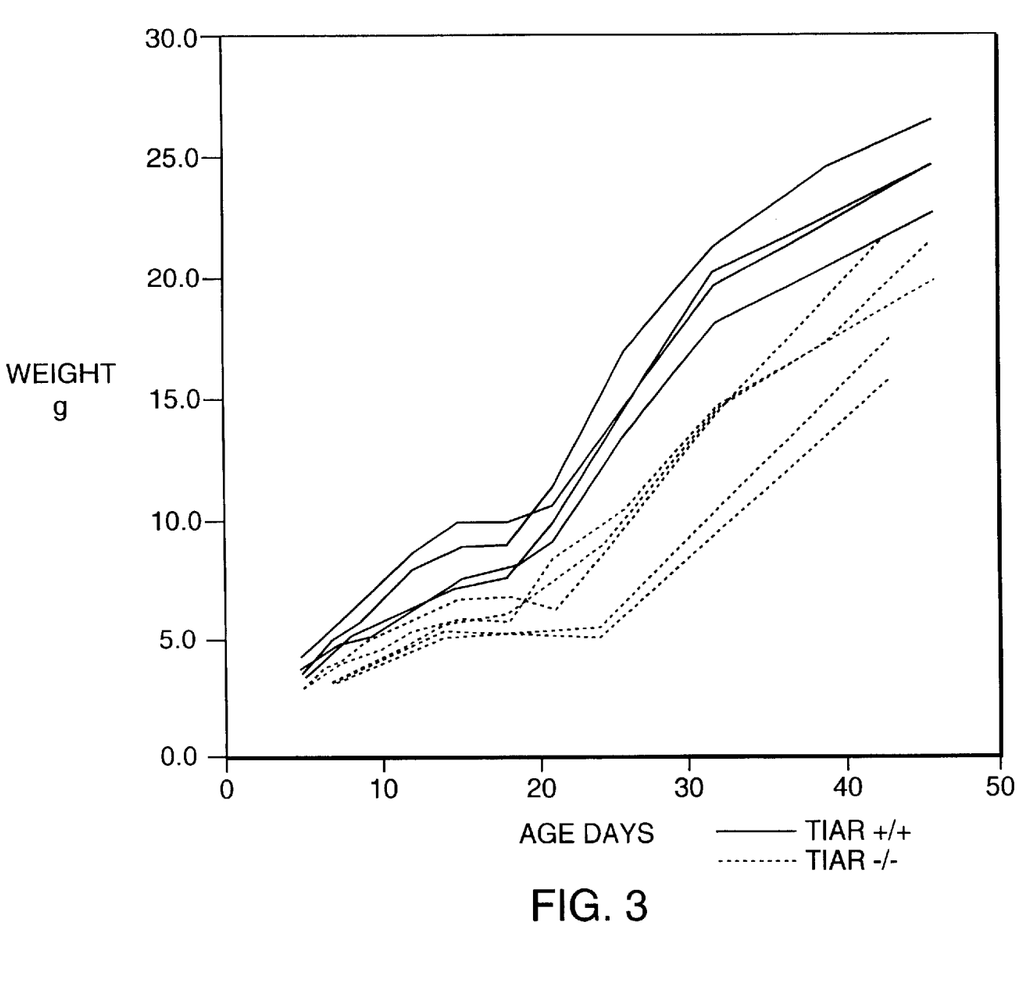
FIG. 3 is a graph showing that TIAR-deficient mice are underweight during early development. "Age day" refers to the number of days post partum.

Beginning between 5–10 days after birth, mice were weighed at intervals of 3–7 days. To keep track of individual mice, they were labeled with color pen markers before permanent labeling at about 20 days of age. The data showed that tiar$^{-/-}$ mice were significantly underweight at birth (FIG. 3). However, a majority of these mice became obese at the age of about 2 to 3 months. The obese mice displayed high blood levels of leptin, and consumed abnormally large amounts of food.

iii) Neurological disorders

The knockout mice displayed an unusual jittery behavior. In response to the mild stress that occurs during routine handling, TIAR$^{-/-}$ mice were generally more agitated (e.g., trying to avoid the procedures) than wild type mice. This agitated behavior developed into uncontrolled shaking in young mice that were 2 to 3 weeks old. The knockout mice could often be differentiated from wildtype or heterozygous littermates by their more undirected movements inside the cage.

When held up by their tails, older knockout mice (e.g., at about 3 months of age or older) typically clutched their hindlegs against the abdomen and did jerking movements with their body, whereas wildtype mice spread out their hindlegs to balance themselves, and appeared to be much calmer.

iv) Infertility

Breedings of either male or female tiar$^{-/-}$ mice with wildtype mice were unsuccessful, indicating that both sexes were sterile. Histologic analysis revealed that the tiar$^{-/-}$ ovaries were slightly smaller than normal and lacked developing follicles and oocytes. The residual ovary showed hyperplasia of sex cord derivatives and underlying stroma in a trabecular and tubular pattern. Continued growth of these elements caused tiar$^{-/-}$ ovaries to grow to approximately five times the size of wildtype ovaries by 8 months. The tiar$^{-/-}$ testes lacked spermatogonia, spermatids, and mature spermatozoa. At three months of age, testes of tiar$^{-/-}$ mice were approximately one-third the normal size. The architecture of the seminiferous tubules was largely normal, and interstitial Leydig cells and Sertoli cells appeared in their expected locations.

The absence of both sperm and eggs in tiar$^{-/-}$ mice suggested a developmental defect at the level of PGCs. Murine PGCs are detected in the extraembryonic mesoderm at E7. They then come to underlie the posterior part of the primitive streak and become incorporated into the base of the allantois. At E8, the PGCs begin to disperse, and by the early somite stage, a majority of the PGCs are found intercalated into the epithelium of the hindgut. The PGCs leave the hindgut and traverse the dorsal mesentery toward the coelomic angles, the first cells reaching the genital ridges by E11–11.5. Their movement from the gut to the genital ridges involves active migratory movements, probably dependent on a suitable substratum and possibly involving chemotactic signals. By E13, approximately 25,000 PGCs have colonized each gonad primordium.

Histology of wildtype and tiar$^{-/-}$ embryos revealed marked differences in the number of PGCs populating the genital ridges at E11.5 and E13.5. PGCs were present at the genital ridge of both wildtype and tiar$^{-/-}$ embryos at E11.5, although the number of PGCs was reduced drastically in tiar$^{-/-}$ embryos. Whereas PGCs proliferated to fully populate the genital ridge of wildtype embryos by E13.5, PGCs were absent from E13.5 tiar$^{-/-}$ embryos. It is unlikely that the migration of tiar$^{-/-}$ PGCs simply was delayed or aberrant, because sectioning of entire embryos did not reveal any unusually located PGCs. The decreased number of PGCs at the genital ridge in tiar$^{-/-}$ embryos could have resulted from the inability of tiar$^{-/-}$ PGCs to respond to a survival signal during migration or on arrival at the genital ridge or could have resulted from the inability of the surrounding tissues to provide a survival signal or both. Although it is likely that PGCs arriving at the genital ridge in tiar$^{-/-}$ mice died by apoptosis, terminal deoxynucleotidyl transferase-mediated dUTP-biotin nick end-labeling (TUNEL) analysis did not detect large numbers of apoptotic cells in these sections. This was probably a consequence of the small numbers of PGCs present at the genital ridge and the rapidity with which apoptotic cells were phagocytosed by neighboring cells.

Consistent with a role for TIAR in PGC development was the high level of TIAR expression in PGC nuclei as determined by immunohistochemistry. Staining of embryo sections with a TIAR-specific mAb revealed that TIAR was expressed highly in selected cells of the developing gonad, brain, neural tube, and ganglia, as well as in certain epithelial cells. Cells in many other tissues exhibited a relatively low level of TIAR expression. Staining of a E14.5 tiar$^{+/+}$ testis showed that TIAR was highly expressed in the nuclei of PGCs contained within seminiferous tubules. In contrast, precursor Sertoli cells lining the seminiferous tubules expressed little or no TIAR. The precursor Leydig cells between the seminiferous tubules expressed relatively low levels of TIAR similar to those found in many tissues throughout the embryo. Staining of a E14.5 tiar$^{-/-}$ testis confirmed the absence of TIAR protein and the specificity of the staining reaction. Wildtype E14.5 testes expressed the PGC-specific antigen GCNA1, confirming (by location and morphology) that cells expressing high levels of TIAR were PGCs. Analysis of a wildtype E12.5 gonad indicated that TIAR expression in PGCs was not stage-specific and presumably occurred throughout development. tiar$^{-/-}$ embryos derived from crosses between tiar$^{+/-}$ mice backcrossed onto BALB/c mice for four generations also lacked PGCs. Taken together, these results demonstrate that TIAR is essential for PGC development.

Several growth factors prolong the survival of PGCs in vitro, including LIF. Because PGCs can be dedifferentiated into ES-like cells in the presence of growth factors, whether TIAR regulates ES cell proliferation was assessed in the presence or absence of exogenous LIF by using an in vitro methylcellulose assay culture system. To this end, two independent tiar$^{-/-}$ ES cell lines as well as control tiar$^{+/+}$ and tiar$^{+/-}$ ES cell lines were cultured in medium containing methylcellulose, which prevents cell-cell interactions, and proliferation was measured by [$^3$H]thymidine incorporation at various times after cell plating. In the absence of LIF, both the tiar$^{-/-}$ and control ES cells grew about equally well and had a similar morphology for the first 2–3 days, but after 3 days, the tiar$^{-/-}$ ES cells stopped proliferating and appeared dead, whereas the controls continued to grow. In the presence of LIF (1,000 units/ml), both the tiar$^{-/-}$ and control ES cells grew about equally well at all time points measured. Proliferation of the tiar$^{-/-}$ and control ES cells was also about the same in the absence of LIF when cells were cultured in medium lacking methylcellulose. Thus, TIAR appears necessary for the clonal outgrowth of ES cells in the absence of exogenous LIF.

II. Cell Lines Derived from Transgenic Animals

Standard techniques known in the art may be used to generate cell lines from the cells of the present transgenic mammals. For instance, primordial germ cell lines can be established by techniques conventionally used for establishing ES cell lines.

III. Use of the Transgenic Animals and Cell Lines Thereof

The present transgenic animals and cell lines derived therefrom can be used in a variety of ways to study the function of the TIAR protein. For instance, one way to study the roles of the various TIAR domains is to reconstitute the above-described TIAR-deficient mice with a mutant TIAR protein lacking a domain of interest.

The present animals and cell lines can also be used to identify compounds that have therapeutic value for infertility, obesity, ovarian sex cord stromal tumors, or certain neurological disorders by standard techniques or modified versions of these techniques.

Other Embodiments

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. A transgenic mouse whose genome is heterozygous for an engineered disruption in a TIAR gene, wherein said engineered disruption in a homozygous state inhibits production of functional TIAR protein resulting in a transgenic mouse which is infertile, is obese, or has an ovarian sex cord stromal tumor.

2. A transgenic mouse whose genome is homozygous for an engineered disruption in a TIAR gene, wherein said engineered disruption in a homozygous state inhibits production of functional TIAR protein resulting in a transgenic mouse which is infertile, is obese, or has an ovarian sex cord stromal tumor.

3. A method of determining whether a compound decreases body weight, the method comprising:
   (a) providing a first and second transgenic mouse each according to claim 2;
   (b) administering a compound to the first transgenic mouse; and
   (c) determining the body weight of the first and second transgenic mouse, wherein a lower body weight of the first transgenic mouse, as compared to the second transgenic mouse, indicates that the compound decreases body weight.

4. A method of determining whether a compound inhibits the development of obesity, the method comprising:
   (a) providing a first and second plurality of trangenic mice each according to claim 2;
   (b) administering a compound to the first plurality of transgenic mice; and
   (c) determining an average body weight of the first and second plurality of transgenic mice after 2 months of age, wherein a lower average bode weight of the first plurality of transgenic mice, as compared to the second plurality of transgenic mice indicates that the compound inhibits obesity.

5. A method of determining whether a compound alters development of ovarian sex cord stromal tumors, the method comprising:
   (a) providing a first and second transcenic mouse each according to claim 2, wherein said first and second transgenic mice have an ovarian sex cord stromal tumor;
   (b) administering a compound to the first transgenic mouse; and
   (c) determining the development of the ovarian sex cord stromal tumor of the first and second transgenic mouse, wherein an alteration in the development of the ovarian sex cord stromal tumor of the first transgenic mouse, as compared to the second transgenic mouse, indicates that the compound alters development of ovarian sex cord stromal tumors.

6. A method of determining whether a compound decreases leptin levels, the method comprising:
   (a) providing a transgenic mouse according to claim 2;
   (b) determining the leptin level of the transgenic mouse;
   (c) administering a compound to the transgenic mouse; and
   (d) determining the leptin level of the transgenic mouse after administering the compound, wherein a lower leptin level in the transgenic mouse after administering the compound, as compared to the leptin level determined in step (b), indicates that the compound decreases leptin levels.

7. A method of determining whether a compound decreases food consumption, the method comprising:
   (a) providing a transgenic mouse according to claim 2;
   (b) determining the food consumption of the transgenic mouse;
   (c) administering a compound to the transgenic mouse; and
   (d) determining the food consumption of the transgenic mouse after administering the compound, wherein a lower food consumption in the transgenic mouse as compared to the food consumption determined in step (b), indicates that the compound decreases food consumption.

8. A cell isolated from the transgenic mouse of claim 2, wherein the genome of the cell comprises a homozygous engineered disruption of a TIAR gene, wherein the disruption of the TIAR gene inhibits production of functional TIAR protein.

9. A primordial germ cell isolated from a transgenic mouse embryo whose genome comprises a homozygous engineered disruption of a TIAR gene wherein the disruption of the TIAR gene inhibits production of functional TIAR protein.

10. The cell according to claim 8 which is a neuronal cell.

11. The cell according to claim 8 which is a fibroblast.

12. The cell according to claim 8 which is an ovarian sex cord stromal tumor cell.

13. A cell line comprising progeny of the cell according to claim 8, wherein the progeny of the cell comprise a homozygous engineered disruption of the TIAR gene wherein the disruption inhibits production of functional TIAR.

14. A cell line comprising progeny of the cell according to claim 9, wherein the progeny of the cell comprise a homozygous engineered disruption of the TIAR gene wherein the disruption inhibits production of functional TIAR.

15. A cell line comprising progeny of the cell according to claim 10, wherein the progeny of the cell comprise a homozygous engineered disruption of the TIAR gene wherein the disruption inhibits production of functional TIAR.

16. A cell line comprising progeny of the cell according to claim 11, wherein the progeny of the cell comprise a homozygous engineered disruption of the TIAR gene wherein the disruption inhibits production of functional TIAR.

17. A cell line comprising progeny of the cell according to claim 12, wherein the progeny of the cell comprise a homozygous engineered disruption of the TIAR gene wherein the disruption inhibits production of functional TIAR.

18. A method of determining whether a compound enhances the growth rate, life span, or differentiation of a primordial germ cell, the method comprising:
   (a) providing a first and second plurality of primordial germ cells each according to claim 9;
   (b) incubating the first plurality of primordial germ cells with a compound; and
   (c) determining the growth rate, life span, or differentiation of the first and second plurality of primordial germ cells, wherein an increase in growth rate, life span, or differentiation of the first plurality of primordial germ cells, as compared to the second plurality of primordial germ cells, indicates that the compound enhances the growth rate, life span, or differentiation of primordial germ cells.

19. A method of determining whether a compound inhibits the growth rate of ovarian sex cord stromal tumor cells, the method comprising:
   (a) providing a first and second plurality of ovarian sex cord stromal tumor cells each according to claim 12;
   (b) incubating the first plurality of ovarian sex cord stromal tumor cells with a compound; and
   (c) determining the growth rate of the first and second plurality of ovarian sex cord stromal tumor cells, wherein an decrease in the growth rate of the first plurality of ovarian sex cord stromal tumor cells, as compared to the second plurality of ovarian sex cord stromal tumor cells, indicates that the compound inhibits the growth rate of ovarian sex cord stromal tumor cells.

20. A method of determining whether a compound enhances the growth rate, life span, or differentiation of primordial germ cells, the method comprising:
   (a) providing a first and second plurality of primordial germ cells each from the cell line of claim 14;
   (b) incubating the first plurality of primordial germ cells with a compound; and
   (c) determining the growth rate, life span, or differentiation of the first and second plurality of primordial germ cells, wherein an increase in growth rate, life span, or differentiation of the first plurality of primordial germ cells, as compared to the second plurality of primordial germ cells, indicates that the compound enhances the growth rate, life span, or differentiation of primordial germ cells.

21. A method of determining whether a compound inhibits the growth rate of ovarian sex cord stromal tumor cells, the method comprising:
   (a) providing a first and second plurality of cells each from the ovarian sex cord stromal tumor cell line of claim 17;
   (b) incubating the first plurality of ovarian sex cord stromal tumor cells with a compound; and
   (c) determining the growth rate of the first and second plurality of ovarian sex cord stromal tumor cells, wherein an decrease in the growth rate of the first plurality of ovarian sex cord stromal tumor cells, as compared to the second plurality of ovarian sex cord stromal tumor cells, indicates that the compound inhibits the growth rate of ovarian sex cord stromal tumor cells.

22. A method of determining whether a compound enhances survival of primordial germ cells, the method comprising:
   (a) providing a first and second transgenic mouse embryo, wherein the genomes of the first and second embryo comprise a homozygous engineered disruption in a TIAR gene, wherein the disruption of the TIAR gene inhibits production of functional TIAR protein;
   (b) administering a compound to primordial germ cells in the first embryo; and
   (c) determining survival of primordial germ cells in the first and second embryos, wherein an increase in survival of the primordial germ cells in the first embryo, as compared to the primordial germ cells in the second embryo, indicates that the compound enhances survival of primordial germ cells.

* * * * *

UNITED STATES PATENT AND TRADEMARK OFFICE
CERTIFICATE OF CORRECTION

PATENT NO. : 6,180,849 B1  Page 1 of 1
DATED : January 30, 2001
INVENTOR(S) : Michel Streuli et al.

It is certified that error appears in the above-identified patent and that said Letters Patent is hereby corrected as shown below:

Title page,
Item [54] "TRANGENIC" should be -- TRANSGENIC --.

Column 9, claim 4,
Line 53, "bode" should be -- body --.

Signed and Sealed this

Eighteenth Day of December, 2001

Attest:

Attesting Officer

JAMES E. ROGAN
Director of the United States Patent and Trademark Office